United States Patent [19]

Kornfeld et al.

[11] B 3,985,752

[45] Oct. 12, 1976

[54] 6-METHYL-8-(SUBSTITUTED) METHYLERGOLINES

[75] Inventors: Edmund C. Kornfeld; Nicholas J. Bach, both of Indianapolis, Ind.

[73] Assignee: Eli Lilly and Company, Indianapolis, Ind.

[22] Filed: Dec. 6, 1974

[21] Appl. No.: 530,318

[44] Published under the second Trial Voluntary Protest Program on January 13, 1976 as document No. B 530,318.

[52] U.S. Cl................................. 260/285.5; 424/262
[51] Int. Cl.².......................................... C07D 519/02
[58] Field of Search................................ 260/285.5

[56] References Cited

UNITED STATES PATENTS

| | | | |
|---|---|---|---|
| 3,557,118 | 1/1971 | Arcamone et al. | 260/285.5 |
| 3,732,231 | 5/1973 | Temonsky et al. | 260/285.5 |

*Primary Examiner*—R. Gallagher
*Assistant Examiner*—James H. Turnipseed
*Attorney, Agent, or Firm*—Charles W. Ashbrook; Everet F. Smith

[57] ABSTRACT

6-Methyl-8-(substituted)methylergolines, useful as prolactin inhibitors.

7 Claims, No Drawings

6-METHYL-8-(SUBSTITUTED) METHYLERGOLINES

BACKGROUND OF THE INVENTION

Pharmacologically active compounds derived from ergotted grain, referred to generically as ergot alkaloids, have been known for centuries. The ergot alkaloids have been shown to possess a wide variety of valuable physiological activities. Almost all of the ergot alkaloids and their derivatives are alike in that they possess the same general tetracyclic ring system represented by the formula

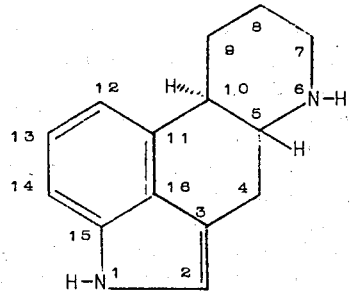

I

Ergot alkaloid compounds containing the above ring system are usually classified into one of two classes: those which are amides of D-6-methyl-8-carboxy-$\Delta^9$-ergoline, (lysergic acid); and those which are derivatives of D-6-methyl-8-methyl-$\Delta^8$ or $\Delta^9$-ergoline, (the clavines). Typically, compounds of the clavine class possess some degree of prolactin inhibitory activity. Because of this unique activity, these compounds are useful in the treatment of prolactin-dependent conditions in which prolactin secretion has an adverse affect.

Numerous semi-synthetic ergot alkaloid derivatives of the clavine class have recently been prepared and shown to possess useful properties. For example, Camerino et al. prepared and evaluated numerous 8-acylaminomethylergolines, as described in U.S. Pat. No. 3,238,211. Erich et al. prepared a wide variety of 8-acyloxymethylergolines which demonstrated strong uterus-contracting action. Additionally, Arcamone et al. prepared a variety of ergoline derivatives, including 8-acylaminomethylergoline derivatives, see U.S. Pat. No. 3,324,133.

It is an object of this invention to provide new ergot alkaloid compounds characterized as being of the clavine class.

SUMMARY OF THE INVENTION

This invention relates to new ergot alkaloid derivatives. More particularly, this invention provides novel 6-methyl-8β-(substituted)methylergolines having the general structural formula

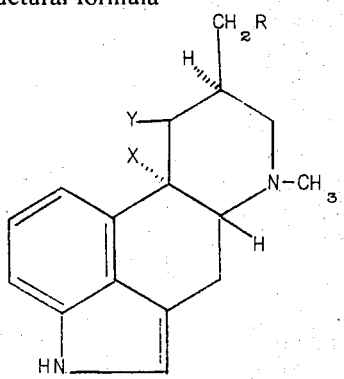

II in which X and Y each are hydrogen or, taken together, form a double bond, and R is $CH_2R_1$, $NHR_2$, nitro, or isocyano, in which $R_1$ is cyano or methylsulfinyl, and in which $R_2$ is methanesulfonyl or formyl. The non-toxic pharmaceutically-acceptable acid addition salts of the bases having the above formula are considered to fall within the scope of this invention.

The compounds provided herein are useful as intermediates leading to other ergot alkaloids, and are particularly useful as prolactin inhibitors.

DETAILED DESCRIPTION OF THE INVENTION

The new compounds provided by this invention are generically described as D-6-methyl-8β-(substituted)-methylergolines. The term "ergoline" as used herein includes compounds of the above formula in which both X and Y are hydrogen and those in which X and Y, taken together, form a double bond. The latter compounds are often referred to as $\Delta^9$-ergolines, or preferably as 9-ergolenes. A preferred group of compounds provided by this invention have the above formula in which both X and Y are hydrogen, and are referred to as D-6-methyl-8β-(substituted)methylergolines. Those compounds having the above formula wherein X and Y, taken together, form a double bond are named as D-6-methyl-8β-(substituted)methyl-9-ergolenes.

Because the novel ergolines and ergolenes provided herein all are characterized as having a substituent in the 8β-position, as evidenced in the above formula by the solid bonding line between $C_8$ of the ergoline ring system and $CH_2R$, the β designation will be omitted hereinafter when naming the compounds of this invention. It will accordingly be understood that all of the compounds of this invention bear an 8β-(substituted)-methyl substituent.

The compounds provided by the present invention can generally be prepared by procedures familiar to those skilled in the art. The starting materials which are employed in the preparation of the new ergolines are known compounds and can be readily prepared by established procedures.

The 6-methyl-8-(substituted)methylergolines represented by the above formula when R is $CH_2R_1$ and $R_1$ is cyano or methylsulfinyl can be prepared by reacting an ergoline having an 8-(substituted)methyl group, wherein the substituent is a readily displaceable leaving group, with a nucleophilic carbanion derived from either acetonitrile or dimethyl sulfoxide. A readily displaceable leaving group is a group that is easily replaced by reaction with a nucleophilic substance. Such readily displaceable leaving groups are well known to organic chemists and normally include, for instance, halogen atoms such as iodine, bromine or chlorine, as well as certain esters, particularly methanesulfonyloxy or p-toluenesulfonyloxy. Typical ergoline starting materials which have a readily displaceable leaving group attached to the 8-methyl substituent include ergolines such as D-6-methyl-8-bromomethylergoline, D-6-methyl-8-chloromethyl-9-ergolene, D-6-methyl-8-bromomethyl-9-ergolene, D-6-methyl-8-iodomethylergoline, D-6-methyl-8-methanesulfonyloxymethyl-9-ergolene, D-6-methyl-8-(p-toluene-sulfonyloxy) methylergoline, and the like. Such suitably substituted ergoline derivatives are well known and are readily available. For example, D-6-methyl-8-chloromethylergoline can be prepared according to the procedure set forth by Semonsky et al., U.S. Pat. No. 3,732,231, and compounds such as 6-methyl-8-mesyloxymethyl-9-ergolene are available by the method of Fehr et al., U.S. Pat. No. 3,821,226.

Accordingly, a suitably substituted ergoline derivative is treated with the carbanion formed by reaction of acetonitrile or dimethyl sulfoxide with a strong base, thereby causing displacement of the readily displaceable leaving group of the suitably substituted ergoline and inserting therefor a substituent represented by $CH_2R_1$ in the above formula, wherein $R_1$ is cyano or methylsulfinyl. The carbanion of acetonitrile and the carbanion of dimethyl sulfoxide are well known reactive derivatives and can be prepared by reaction of acetonitrile or dimethyl sulfoxide, respectively, with any of a number of strong bases, including sodium hydride, n-butyl lithium, lithium methoxide, lithium diisopropylamide, or the like.

The reaction of the suitably substituted ergoline, for example 6-methyl-8-bromomethyl-9-ergolene, and the carbanion of acetonitrile or dimethyl sulfoxide is generally carried out in a non-aqueous solvent. Typical solvents commonly used for such displacement reactions include diethyl ether, tetrahydrofuran, dioxane, and related solvents. The displacement reaction is generally conducted at a temperature in the range of about −70° to 100°C., and the reaction is usually substantially complete within about 1 to 30 hours. The product can be isolated as a free base or as an acid addition salt by proper adjustment of the pH. In a typical isolation procedure, for example, the alkaline reaction mixture can be diluted with water, and the water-insoluble product can be extracted therefrom with any of a number of water-immiscible organic solvents, including diethyl ether, ethyl acetate, chloroform, and the like. Evaporation of the organic solvent provides the novel compound of this invention as the free base, which can be further purified if desired by general methods such as recrystallization, chromatography, salt formation, and the like.

Compounds having the above formula in which R is a nitro group are prepared by substantially the same procedure as that described hereinabove. For instance, an ergoline having a readily displaceable group substituted on the 8-methyl substituent is treated with sodium nitrite in an organic solvent such as dimethylformamide or dimethyl sulfoxide. Typical ergolines commonly used as a starting material include D-6-methyl-8-(p-toluenesulfonyloxy)methylergoline, D-6-methyl-8-(p-toluenesulfonyloxy) methyl-9-ergolene, D-6-methyl-8-bromomethylergoline, and related compounds. The nitrite displacement reaction is generally carried out at a temperature ranging from about 0° to 100°C., and is usually complete within 30 to 90 hours. As described hereinbefore, the product, presently an 8-nitromethylergoline derivative, can be isolated as a free base or as an acid addition salt, and normal purification procedures such as crystallization or chromatography can be carried out if desired.

Further, in accordance with the present invention, compounds having the above formula wherein R is a substituted amino group are prepared by reacting an 8-aminomethylergoline with an acylating agent. The 8-aminomethylergoline starting materials, such as D-6-methyl-8-aminomethylergoline for instance, are readily available by the method of Camerino et al. as described in U.S. Pat. No. 3,238,211. The acylating agents which are reacted with the aminomethyl ergolines include compounds such as methanesulfonyl chloride, p-toluenesulfonyl chloride, chloral, acetyl chloride, and the like. Typically, the acylation of the aminomethylergoline is carried out in a solvent such as benzene, xylene, toluene, chloroform, or the like. An added base, such as pyridine or triethylamine for instance, also can be present if desired, and if present, serves as an acid-binding agent. The reaction is customarily carried out at a temperature of about 0° to 100°C., and is routinely complete within ½ to 8 hours. The product is generally isolated by diluting the reaction mixture with water and extracting the water-insoluble product therefrom with a water-immiscible solvent such as ethyl acetate or diethyl ether. The isolated product can be further purified if desired by recrystallization, chromatography, salt formation, and similar purification techniques commonly used in chemistry.

The 8-(N-formyl) aminomethylergolines, compounds having the above formula wherein R is $NHR_2$ and $R_2$ is formyl, which compounds are prepared by reaction of an 8-aminomethylergoline with chloral as described hereinbefore, can be converted to the corresponding 8-isocyanomethylergoline, compounds having the above formula in which R is isocyano. The conversion is accomplished by general procedures comprising reacting the 8-(N-formyl) aminomethylergoline with a halogenating agent such as thionyl chloride, phosphorous oxychloride, or phosgene, in the presence of a base such as triethylamine, potassium tert.-butoxide, sodium carbonate, pyridine, or the like. The reaction is generally accomplished by reacting the ergoline starting material, such as D-6-methyl-8-(N-formyl) aminomethyl-9-ergolene for example, with a halogenating agent in an organic solvent such as dimethylformamide, dimethyl sulfoxide, chloroform, pyridine, or the like. The reaction is typically carried out at a temperature ranging from about −70° to 50°C., and is generally substantially complete within about 15 to 30 hours. The product is customarily isolated by adding water to the reaction mixture and extracting the product therefrom with a water-immiscible solvent such as ethyl acetate or diethyl ether. The isonitrile so formed can be further purified if needed by recrystallization or chromatography. Alternatively, the 8-isocyanomethylergoline can be converted to a non-toxic pharmaceutically-acceptable salt by reaction with a suitable acid in the normal manner as described hereinbelow.

The compounds provided by this invention generally exist as white crystalline solids. They readily form non-toxic, pharmaceutically-acceptable acid addition salts with any of a number of acids, including inorganic acids and organic acids. Commonly used inorganic acids are mineral acids such as hydrochloric, sulfuric, phosphoric, hydrobromic, hydroiodic, nitric, and related acids. Additionally, salts can be formed by reaction of the ergot alkaloid derivative with an organic acid such as methanesulfonic, p-toluenesulfonic, n-butyric, isobutyric, malonic, benzoic, maleic, succinic, phenylacetic, p-hydroxyphenylacetic, and like acids.

Generally, pharmaceutically-acceptable acid addition salts of the ergolines having the above formula are prepared by established procedures, such as reacting the ergoline base with a one equivalent amount of an acid, or an excess of acid if desired. The reaction is typically carried out in a solvent such as diethyl ether, ethyl acetate, tetrahydrofuran, or the like. Alternatively, the acid addition salt can be formed by proper adjustment of the pH of the reaction mixture by the addition of a suitable acid, and isolation therefrom of the corresponding salt.

As hereinbefore indicated, the new ergolines of this invention are useful as inhibitors of prolactin. For example, the compounds provided herein are potentially useful in the treatment of inappropriate lactation, such as undesired postpartum lactation, and galactorrhea. Additionally, the new compounds of the present invention are potentially useful in treating prolactin-dependent adenocarcinomas, prolactin-secreting pituitary tumors, and the like.

The new ergolines of this invention, including the pharmaceutically-acceptable salts thereof, can be administered to a subject to inhibit prolactin secretion. The compound can be suitably formulated and administered parenterally or orally to a subject in amounts varying from about 0.01 to about 10 mg. per Kg. of body weight from one to four times each day. The new compounds provided herein are especially suited to oral administration, and are preferably formulated for oral administration and supplied as tablets, suspensions, or in capsules. Parenteral administration can be effected by formulating the new compounds for injection subcutaneously, intravenously, intramuscularly, and the like. The compounds provided herein will be formulated in standard procedures utilizing common diluents, excipients, and carriers such as starch, lactose, talc, magnesium stearate, or other excipients commonly employed in pharmacy.

The following detailed examples are provided, setting forth representative embodiments of the present invention. The examples should not, however, be construed as limiting the invention to the particular aspects set forth therein.

EXAMPLE 1

D-6-Methyl-8-(2-cyanoethyl) ergoline

A solution of 1.28 ml. of acetonitrile in 20 ml. of tetrahydrofuran was stirred under a nitrogen atmosphere and cooled to −60°C. in a dry ice-acetone bath. A solution of 1.54 g. of n-butyl lithium in 15 ml. of hexane was added in one portion, and the reaction mixture was stirred for 15 minutes at −60°C. A solution of 975 mg. of D-6-methyl-8-bromomethylergoline in 50 ml. of tetrahydrofuran was added dropwise to the reaction mixture. The reaction mixture was stirred for 30 minutes at −60°C. and for 90 minutes at 0°C. The reaction mixture was then added to 100 ml. of water, and the water-insoluble product was extracted therefrom into ethyl acetate. The combined organic extracts were washed with saturated aqueous sodium chloride solution, dried, and the solvent was removed under reduced pressure to provide an oil. The oil was applied to a column packed with 25 g. of florisil, and eluted with chloroform. Eluate fractions shown to contain the desired product by thin layer chromatography were combined and the solvent was removed therefrom under reduced pressure, affording D-6-methyl-8-(2-cyanoethyl) ergoline. M.P. 222°–223°C.

Analysis Calc. for $C_{18}H_{21}N_3$: Theory: C, 77.38; H, 7.58; N, 15.04; Found: C, 77.27; H, 7.28; N, 15.27.

EXAMPLE 2

D-6-Methyl-8-(2-methylsulfinylethyl) ergoline

A solution of 2.4 g. of sodium hydride in 60 ml. of dimethylsulfoxide was stirred under a nitrogen atmosphere and heated at 80°C. for 30 minutes. The reaction mixture was cooled to about 25°C. and a suspension of 1.44 g. of D-6-methyl-8-chloromethylergoline in 100 ml. of dimethyl sulfoxide was added dropwise over 60 minutes. The reaction mixture was stirred under a nitrogen atmosphere at ambient temperature for three and one half hours. The reaction mixture was cooled to 5°C. in an ice-water bath, and 100 ml. of water was added. The aqueous reaction mixture was extracted with dichloromethane, and the combined organic extracts were washed with water, dried, and the solvent was removed therefrom under reduced pressure, providing a foam. The foam was recrystallized from ethanol to afford D-6-methyl-8-(2-methylsulfinylethyl)ergoline. M.P. 203°–205°C.

Analysis Calc. for $C_{18}H_{24}N_2OS$: Theory: C, 68.32; H, 7.64; N, 8.85; S, 10.13; Found: C, 68.07; H, 7.71; N, 9.00; S, 10.49.

EXAMPLE 3

D-6-Methyl-8-(N-formyl)aminomethylergoline

A solution of 610 mg. of D-6-methyl-8-aminomethylergoline in 100 ml. of benzene was stirred at 24°C. while 675 mg. of chloral hydrate was added in one portion. The reaction mixture was stirred under a nitrogen atmosphere and heated at reflux for four hours in a flask equipped with a Dean-Stark trap for water removal. The reaction mixture was cooled to room temperature, and the reaction solvent was removed under reduced pressure to provide the product as an oil. The oil was crystallized from chloroform and hexane, affording D-6-methyl-8-(N-formyl)aminomethylergoline.

Analysis Calc. for $C_{17}H_{21}N_3O$: Theory: C, 72.06; H, 7.47; N, 14.83; Found: C, 71.82; H, 7.36; N, 14.62.

EXAMPLE 4

D-6-Methyl-8-isocyanomethylergoline

A solution of 1 g. of D-6-methyl-8-(N-formyl)aminomethylergoline in 25 ml. of dimethylformamide was stirred under a nitrogen atmosphere and cooled to −50°C. in a dry ice-ethanol bath. A solution of 400 mg. of thionyl chloride in 10 ml. of dimethylformamide was added dropwise over 30 minutes to the reaction mixture. The reaction mixture was stirred and warmed to −32°C., and 850 mg. of sodium carbonate was added in one portion. The reaction mixture was warmed to about 24°C. and stirred for 20 hours. The reaction mixture was then added to 100 ml. of water, and the product was extracted from the aqueous solution into chloroform. The combined organic extracts were washed with water, dried, and the solvent was removed therefrom under reduced pressure to provide an oil. The oil was crystallized from chloroform and ligroin to afford D-6-methyl-8-isocyanomethylergoline. M.P. 250°–255°C.

Analysis Calc. for $C_{17}H_{19}N_3$: Theory: C, 76.95; H, 7.22; N, 15.84; Found: C, 76.93; H, 7.24; N, 15.54.

EXAMPLE 5

D-6-Methyl-8-nitromethylergoline

A solution of 1.07 g. of D-6-methyl-8-(p-toluenesulfonyloxymethyl)ergoline in 25 ml. of dimethyl sulfoxide containing 1.5 g. of sodium nitrite was stirred under at nitrogen atmosphere at 25°C. for 46 hours. The reaction mixture was poured into 100 ml. of water, and the water-insoluble product was extracted therefrom into ethyl acetate. The organic extracts were combined, washed with aqueous saturated sodium chloride, solution, dried, and the solvent was removed therefrom under reduced pressure, thereby providing the product as a foam. The foam was applied to a chromatography column packed with 50 g. of florisil, and eluted with chloroform. Eluate fractions shown to contain the desired product by thin layer chromatography were combined, and the solvent was removed therefrom under reduced pressure, affording D-6-methyl-8-nitromethylergoline. M.P. 263°–265°C. dec.

Analysis Calc. for $C_{16}H_{19}N_3O_2$: Theory: C, 67.35; H, 6.71; N, 14.73; Found: C, 67.09; H, 6.81; N, 14.93.

EXAMPLE 6

D-6-Methyl-8-(2-cyanoethyl)ergoline maleate

A solution of 2.79 g. of D-6-methyl-8-(2-cyanoethyl)-ergoline, prepared as described in Example 1 above, in 30 ml. of ethyl acetate was stirred while 0.58 g. of maleic acid was added in one portion. The reaction mixture was stirred for 30 minutes and then filtered, providing D-6-methyl-8-(2-cyanoethyl)ergoline maleate as a crystalline solid.

EXAMPLE 7

D-6-Methyl-8-nitromethylergoline hydrochloride

A solution of 2 g. of D-6-methyl-8-nitromethylergoline, prepared as described in Example 5 above, in 50 ml. of diethyl ether was stirred while excess hydrogen chloride gas was bubbled into the reaction mixture. The reaction mixture was filtered, affording D-6-methyl-8-nitromethylergoline hydrochloride as a white crystalline solid.

We claim:

1. A compound of the formula

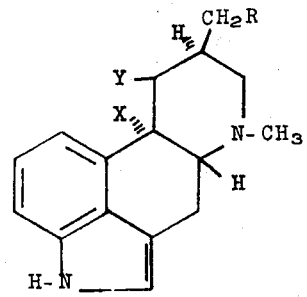

wherein:
X and Y each are hydrogen or, taken together, form a double bond;
R is nitro, isocyano, or $CH_2R_1$;
wherein:
$R_1$ is methylsulfinyl;
and the non-toxic pharmaceutically-acceptable acid addition salts thereof.

2. A compound of claim 1 wherein X and Y each are hydrogen.

3. A compound of claim 1 wherein X and Y taken together form a double bond.

4. The compound of claim 2 wherein R is nitro.

5. The compound of claim 2 wherein R is isocyano.

6. The compound of claim 2 wherein R is $CH_2R_1$.

7. A compound of claim 1 as the non-toxic pharmaceutically-acceptable acid addition salt.

* * * * *